United States Patent [19]

Palatnik

[11] Patent Number: 5,558,096
[45] Date of Patent: Sep. 24, 1996

[54] BLOOD PULSE DETECTION METHOD USING AUTOCORRELATION

[75] Inventor: Eugene S. Palatnik, Pewaukee, Wis.

[73] Assignee: Biochem International, Inc., Waukesha, Wis.

[21] Appl. No.: 505,502

[22] Filed: Jul. 21, 1995

[51] Int. Cl.$^6$ ....................................................... A61B 5/02
[52] U.S. Cl. ......................... 128/687; 128/689; 128/706
[58] Field of Search ................................... 128/632, 633, 128/664–8, 672–5, 680, 687, 689, 696, 706; 364/413.01, 413.02, 413.05; 356/39, 40, 41

[56] References Cited

U.S. PATENT DOCUMENTS

| 4,463,425 | 7/1984 | Hirano et al. | 128/704 |
| 4,621,643 | 11/1986 | New, Jr. et al. | 128/633 |
| 5,249,576 | 11/1993 | Goldberger et al. | 128/632 |

OTHER PUBLICATIONS

Lathi, B. P., "Modern Digital and Analog Communication Systems," Holt, Rinehart and Winston, Inc., Philadelphia, 1989, p. 105.

*Primary Examiner*—Angela D. Sykes
*Assistant Examiner*—Bryan K. Yarnell
*Attorney, Agent, or Firm*—Quarles & Brady

[57] ABSTRACT

A medical monitor determines the period of a physiological function, such as blood circulation pulses, by operating a probe that produces an electrical signal which corresponds to the physiological function. The electrical signal is digitized at a given sampling rate to acquire a plurality of signal samples which are stored in a memory. A time scaling factor is adjusted dynamically so that the amount of signal samples being processed does not exceed a maximum limit. The magnitude of the signal samples also may be scaled dynamically. Serial autocorrelation is applied to the signal samples to produce a sequence of summation values. The quantity of summation values from the initial one in the sequence to a peak summation value is determined. The physiological function period is derived from the quantity of summation values, the given sampling rate, and any time scaling factor that was used.

18 Claims, 6 Drawing Sheets

BLOOD PULSE DETECTION METHOD USING AUTOCORRELATION

BACKGROUND OF THE INVENTION

The present intention relates to medical apparatus for monitoring physiological functions; and more particularly to such apparatus which detect a patient's blood pulse rate and period from circulatory data.

Pulse oximetry is a non-invasive technique which is useful for measuring arterial oxygen saturation and pulse rate. In pulse oximetry, light is passed through a portion of a patient's body, such as a finger, which contains arterial blood flow. An optical sensor detects the light which has passed through the body and the variations in the detected light at various wavelengths then are used to determine arterial oxygen saturation and pulse rates. For example, U.S. Pat. No. 5,437,275 illustrates an optical finger probe for a pulse oximeter which produces an electrical signal indicative of the arterial blood flow. Pulse rates also can be detected by conventional invasive and non-invasive blood pressure monitoring equipment. Sensors have been developed to produce electrical signals indicative of these other physiological functions.

All of these types of equipment produce and analyze an electrical signal having a periodic waveform that corresponds to the physiological function being monitored. Although the signal does not fluctuate significantly between consecutive cycles, the amplitude, frequency and shape of the periodic waveform can vary significantly among different persons depending upon their physical robustness and health. The frequency, amplitude and shape of the signal representing the physiological function of the same person also can vary greatly depending upon the level of physical activity and health at any moment in time.

One of the difficulties encountered in extracting information about the particular physiological function from the corresponding electrical signal is the effect that noise has on the signal. Noise can come from a number of sources including electrical noise produced in the sensors and amplifiers that process the electrical signal, as well as physical effects such as movement of the patient during the examination. For example, derivation of pulse rate from the periodic signal produced by the probe of a pulse oximeter can be affected greatly by movement of the finger to which the probe is attached. Such movement may produce a spurious electrical pulse in the signal from the probe, which may be misinterpreted as being produced by arterial blood flow and thus materially affect the pulse rate determination.

SUMMARY OF THE INVENTION

A general object of the present invention is to provide a method for monitoring the period and rate of a physiological function, such as circulation.

Another object is to derive the period and rate in a manner which provides a high degree of noise immunity.

A further object of the present invention is to derive the physiological function information in real-time.

Still another object of the present invention is to provide such apparatus which can operate over a wide range of rates and intensities of the physiological function.

Yet another object of the present invention is to provide a mechanism which utilizes microprocessor based circuitry in a manner which efficiently uses processing time and a minimal amount of memory.

These an other objects are fulfilled by a medical apparatus which monitors a physiological function of a patient. The apparatus has a probe which produces an electrical signal that varies in correspondence with the physiological function. The electrical signal is sampled at a given sampling rate to acquire a plurality of signal samples X(i), where i is an integer that designates a particular signal sample. As each signal sample is acquired, it is stored in a memory.

In the preferred embodiment of the medical apparatus the amount of memory required is economized by dynamically scaling the signal sample magnitudes and the number of signal samples that have to be processed to determine the period of the physiological function. When a new signal sample exceeds a maximum magnitude value, an amplitude scaling factor $f_A$ is increased, and that new signal sample and all signal sample acquired thereafter are divided by the amplitude scaling factor. The magnitudes of all previously acquired signal samples are adjusted to correspond to the new amplitude scaling factor. When the medical apparatus is unable to determine the period of the physiological function after a predefined number of signal samples have been acquired, a time scaling factor $f_T$ is doubled. The time scaling factor is an integer and thereafter every $f_T$th signal sample is used in monitoring the physiological function. For example, when the time scaling factor is increased from one to two, every other signal sample will be used.

A serial autocorrelation process is applied to the plurality of signal samples and produces a sequence of summation values S(n), where n is a positive integer which designates a particular summation value and the order of the summation values in the sequence. Preferably the sequence of summation values S(n) is produced according to the function:

$$S(n) = f_T f_A^2 \sum_{f_T m=n}^{k} X(f_T m) \cdot X(f_T m - n)$$

where k is the number of probe signal samples that have been accumulated since the last reset of the autocorrelation procedure. The sequence of summation values also is stored in the memory.

A peak summation value S(max), where max is a positive integer, is located in the sequence and the number of summation values from an initial summation value in the sequence to the peak summation value S(max) is determined. That number of summation values corresponds to the physiological function period which is derived by multiplying the number of summation values, the sampling rate and the time scaling factor. The derived physiological function period then is stored in memory and displayed by the preferred embodiment of the medical apparatus.

Specific processes for implementing the autocorrelation and period determination procedures are presented. Also described are processes for determining when noise corrupts the electrical signal to such a degree that the present method is unable to accurately determine the period of the physiological function being monitored.

DETAILED DESCRIPTION OF THE INVENTION

The present invention will be described in the context of a pulse oximeter, although the procedure has equal application in other types of biomedical equipment for measuring physiological functions, such as invasive and non-invasive blood pressure monitors. With initial reference to FIG. 1, the pulse oximeter 10 includes a conventional probe 12 for placement against the body of the patient being monitored. For example, probe 12 can be an electro-optical finger probe as described in the aforementioned U.S. patent. When activated by a driver 11, the probe 12 produces an electrical signal on line 13 which corresponds to the blood flow through the finger of the patient. The probe signal is amplified and filtered by a conventional analog conditioning circuit 14 which produces an output that is applied to an input of an analog-to-digital converter 15 that digitizes the conditioned probe signal. The analog-to-digital converter 15 produces digital samples of the analog probe signal at a 120 Hz. rate, for example, although other sampling rates can be used.

Figure 1:
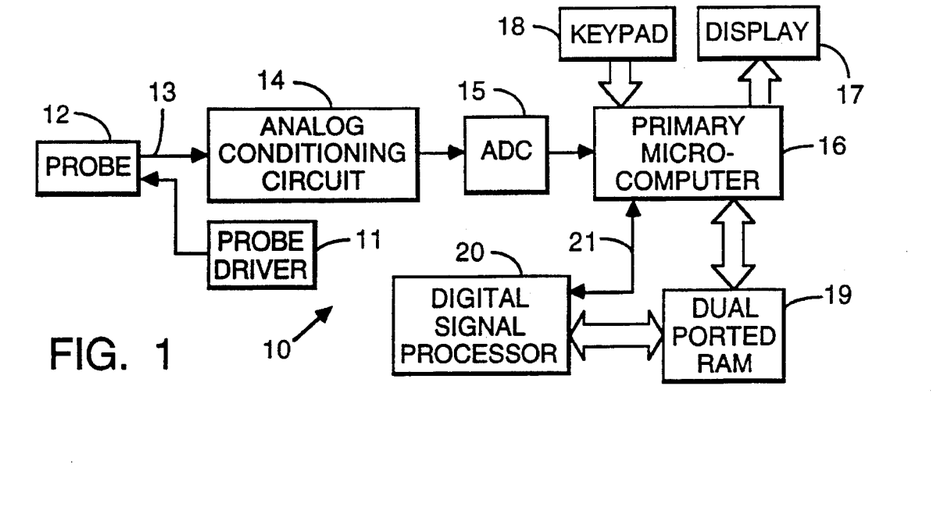
FIG. 1 is a block schematic diagram of a pulse oximeter that incorporates the present invention.

The resultant digitized signal samples are fed to an input port of a primary microcomputer 16. The primary microcomputer 16 contains an internal microprocessor, a random access memory for temporary storage of data and intermediate processing values, and a read only memory which stores the program instructions to be executed by the microprocessor. A separate dual ported random access memory (RAM) 19 is connected to the primary microcomputer 16 for storage of the processed digital signal samples from the probe 12, as well as other data. The primary microcomputer 16 also is connected to an alphanumeric display 17 and a key pad 18 which provide a user interface to the oximeter 10.

Because of the significant amount of data processing which must be carried out by the pulse oximeter 10 and the need to process the data in real-time, a separate digital signal processor 20 is provided. The digital signal processor 20 may be a model ADSP-2105 manufactured by Analog Devices, Inc. of Norwood, Mass., which has an internal microprocessor, random access memory, and read only memory for program storage. The digital signal processor 20 can retrieve and store data within the dual ported RAM 19 so that data can be exchanged with the primary microcomputer 16. Control lines 21 extend between the primary microcomputer 16 and the digital signal processor 20 to coordinate their operation, especially with respect to access to the dual ported RAM 19.

In order to use the pulse oximeter 10, a technician places the probe 12 on a patient's finger and activates the apparatus by means of the key pad 18. The probe driver 11 energizes a light source within the probe 12 to transmit a beam of light through the patient's finger to a detector. The electrical signal produced by the detector is amplified and filtered by the analog conditioning circuit 14 before being digitized by the analog-to-digital converter 15. As noted previously, the analog-to-digital converter produces digitized signal samples at a fixed 120 Hz. rate. As each signal sample is produced by the analog-to-digital converter 15, the primary microcomputer 16 receives the sample and stores it within a sample array in the dual ported RAM 19. The primary microcomputer 16 then transmits a signal to the digital signal processor 20 via lines 21 indicating that a new probe signal sample has been stored.

Upon being notified of a new signal sample, the digital signal processor 20 analyzes the sample to determine whether it is valid and thus can be used in the determination of the blood circulation pulse period and rate. That procedure for monitoring a physiological function is represented in the functional diagram of FIG. 2 and begins with applying serial autocorrelation 30 to the new probe signal sample X(k). Specifically, the serial autocorrelation calculates a sequence of summation values S(n) where n is an index designates a particular one of the summation values and the order of the summation values in sequence. For example, the serial autocorrelation process produces a maximum of 128 summation values, i.e., the initial summation value is designated by an index of zero (n=0) and the last summation value by an index n equal to 127. Although a different quantity of summation values may be utilized, 128 summation values has been found to provide sufficient accuracy and results in considerable conservation of memory space and processing time.

Figure 2:
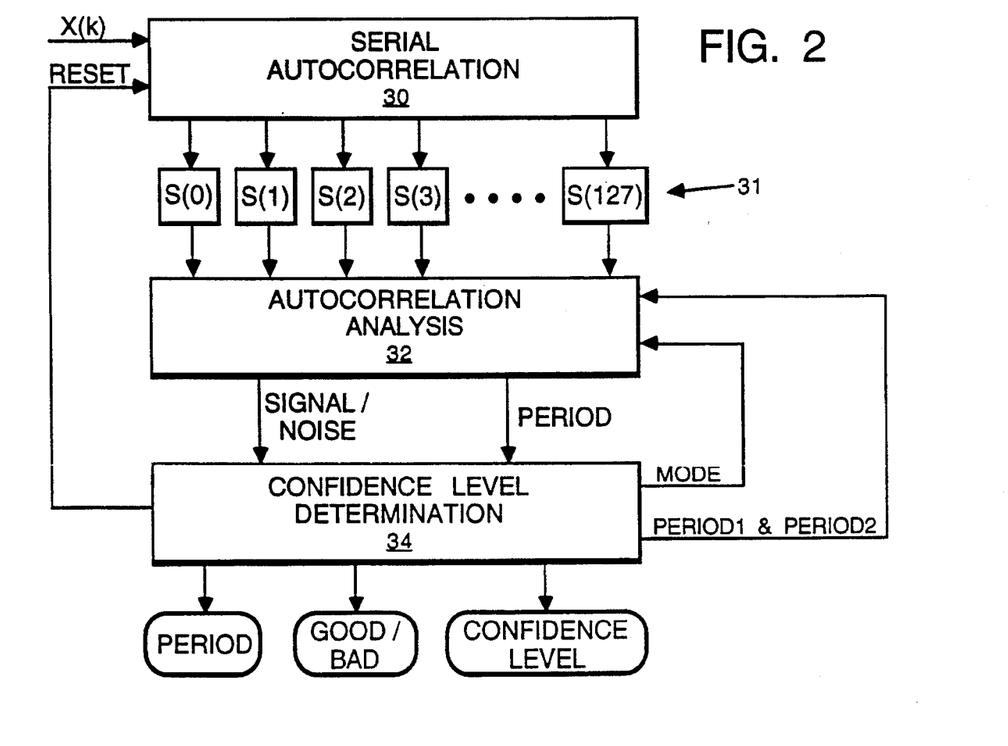
FIG. 2 is a diagram of a procedure by which the oximeter determines blood circulation pulse period and rate.

The autocorrelation process 30 produces the plurality of summation values S(n) according to the general function:

$$S(n) = \sum_{i=n}^{k} X(i) \cdot X(i-n) \quad (2)$$

where k is the number of probe signal samples that have been accumulated since the last reset of the autocorrelation process. Summation value S(0) is referred to as the power of the probe signal and represents a summation of the squares of all signal samples. Summation value S(1) is the power of cross-correlation of the signal with itself shifted by one. Summation value S(2) is the power of cross-correlation of the signal with itself shifted by two, and so on for each additional summation value. It should be noted that when less than 128 signal samples have been accumulated (K<127), the magnitudes of the summation values with indices n greater than k are equal to zero. However, as each additional valid sample of the probe signal is acquired, another summation value will have a non-zero value. A variable designated ST stores the index of highest summation value with a non-zero value.

Figures 3, 4:
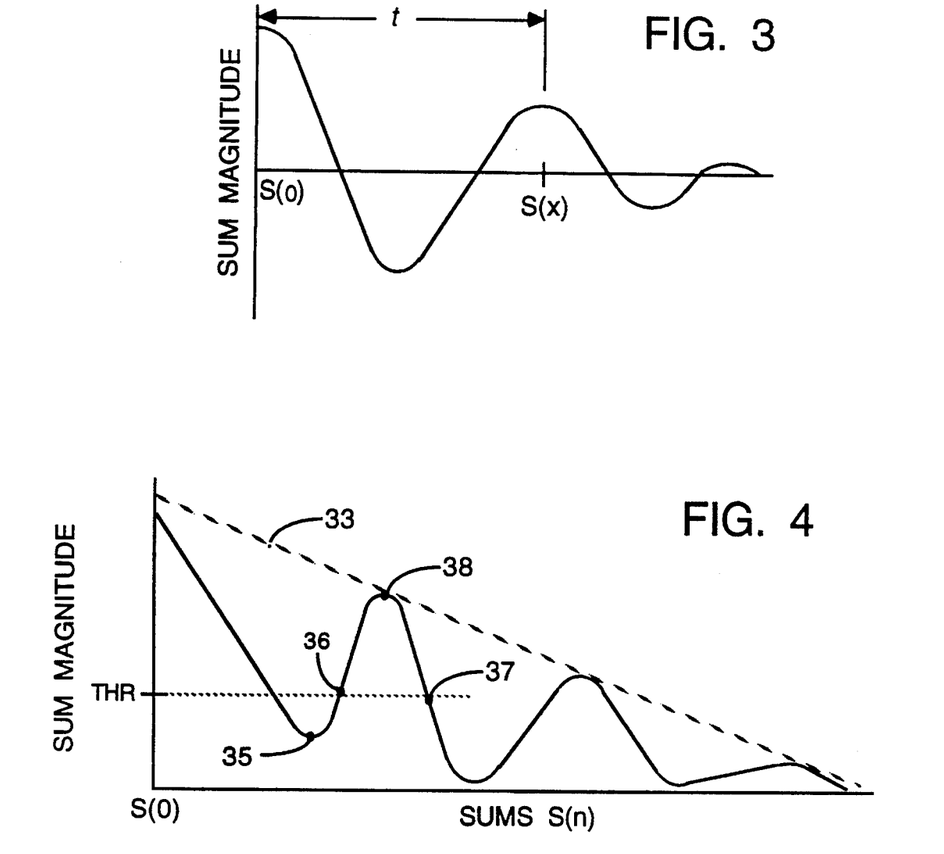
FIG. 3 is a graph depicting an autocorrelation process applied to a sinusoidal signal.
FIG. 4 is a graph illustrates autocorrelation applied to a pulse oximeter probe signal having noise.

FIG. 3 graphically represents the summation values of signal samples for a sinusoidal waveform. As can be seen, the plot has two maximum peaks one at summation value S(0) and another at summation value S(x). The signal sample X(x) occurred one signal cycle period after the initial sample X(0) that was used in the autocorrelation process. Therefore, by knowing the value of index (x) and the sampling rate, the frequency and period of the sinusoidal signal can be determined.

However, the signal produced by the oximeter pulse probe 12 is not purely sinusoidal due to noise effects and physiological factors. As a consequence, a plot of the summation values S(n) over several cycles of the blood circulation produces a waveform similar to that in FIG. 4. This waveform is commonly referred to as being triangular in that the peak summation values decrease linearly as indicated by dashed line 33. Nevertheless, the blood pulse period and rate can be determined using two consecutive peaks of the summation values.

In order to determine the blood circulation pulse period and rate, samples of the pulse probe signal must be acquired over at least one full circulatory cycle. However, the number of signal samples (at the 120 Hz. sampling rate of digital analog converter 15) that are thus required varies greatly among patients, because the blood pulse period differs significantly depending on the patient's health, activity level and other factors. For example, a patient with a relatively slow heart rate requires accumulation of a greater number of signal samples than an individual with a rapid heart rate. The greater the number of signal samples that are required, the larger the memory needed to store the samples and the corresponding summation values, and the greater the computing time required for autocorrelation.

The amplitude of the probe signal also varies significantly depending upon the robustness of the patient being monitored. For example, a sick, weak patient produces an output signal from the pulse probe 12 that has a relatively small peak to peak excursion, whereas a healthy, physically fit individual may produce a pulse probe signal having a very large peak to peak excursion. In order to process signals with very large excursions, relatively large digital values for the signal samples must be accommodated which increases the size of the memory as larger bit digital numbers must be stored at each location. However, the present application allows a reduced amount of memory to be utilized by providing automatic and dynamic scaling of the digital sample magnitudes and of the effective sampling rate.

Figure 5:
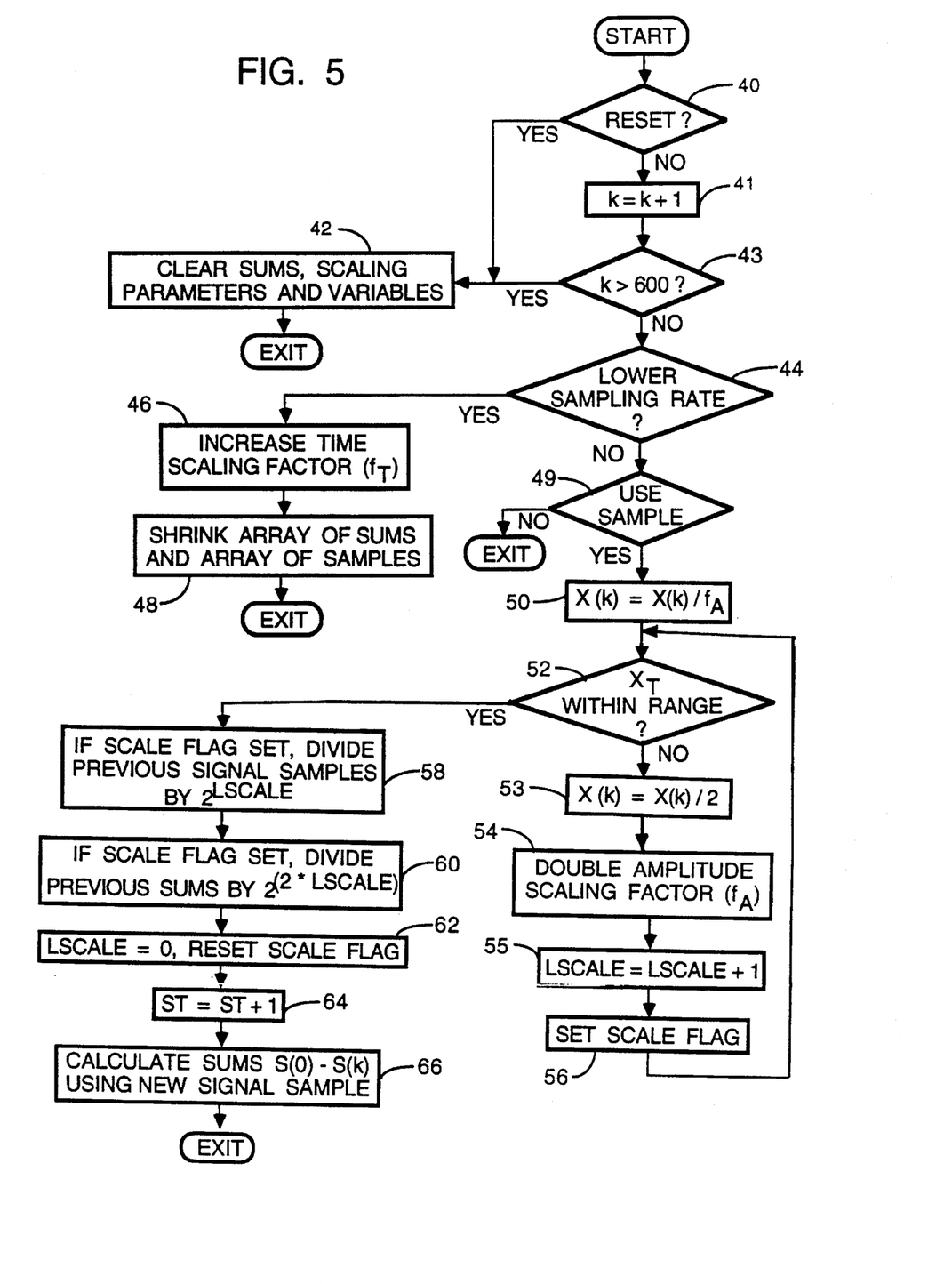
FIG. 5 is a flow chart of an autocorrelation process executed by a digital signal processor in FIG. 1.

With reference to FIG. 5, the serial autocorrelation process 30 is performed by the digital signal processor 20 executing the depicted software routine each time the primary microcomputer 16 stores a new signal sample in the dual ported RAM 19. The execution of that routine commences at step 40 where the digital signal processor 20 checks the RESET indicator from a confidence level determination process 34 which designates whether the serial autocorrelation should be reset. If that is the case, the digital signal processor 20 advances to step 42 where the summation values S(0) through S(127) are zeroed and other variables used in the serial autocorrelation process are initialized. The serial autocorrelation process 30 then terminates until another signal sample is stored in the dual-ported RAM.

If at step 40, the digital signal processor 20 does not find a true RESET indicator, the serial autocorrelation routine advances to step 41 where the count, k, of signal samples is incremented. The new count is compared at step 43 to an absolute maximum amount, for example 600, corresponding to a pulse rate of thirty beats per minute which is well below the rate necessary to keep a human alive. When that amount of samples is exceeded without being able to determine the pulse period, an error is declared and the autocorrelation process is reset. If the count of signal samples is below that maximum limit, the process advances to step 44 where a determination is made whether the effective sampling rate needs to be decreased. If 128 samples have been acquired since the last reset of the autocorrelation process, 128 summation values (ST=127) will have been generated. Since the digital signal processor's internal memory has been configured for an array of summation values of no more than 128, the maximum number of summation values now has been reached. In order to accommodate blood pulse periods which are longer than 128 samples, the effective sampling rate must be effectively decreased. This is accomplished not by decreasing the sampling frequency (120 Hz.) of the analog-to-digital converter 15, but rather by utilizing half the previous number of signal samples provided by the analog-to-digital converter. Thus, the first time that the sampling rate is lowered, only every other digital sample of the pulse probe signal will be utilized.

This is carried out by branching to step 46 where a time scaling factor $f_t$ is increased by two. This time scaling factor is set to an initial value of one whenever the serial autocorrelation is reset. However, one cannot merely begin using every other sample in the middle of the serial autocorrelation process without adjusting the previously calculated summation values, thus every odd numbered summation value, S(1), S(3), S(5), . . . is discarded at step 48, along with all of the previous odd numbered signal samples, X(1), X(3), X(5), . . . . The remaining even numbered signal samples and summation values then are shifted to shrink their respective data arrays as depicted in the following table.

| Signal Samples | Summation Values |
| --- | --- |
| X(0) = X(0), | S(0) = S(0) |
| X(1) = X(2), | S(1) = S(2) |
| X(2) = X(4), | S(2) = S(4) |
| X(3) = X(6), | S(3) = S(6) |
| ⋮ | ⋮ |
| X(63) = X(126), | S(63) = S(126) |

After each array has been shrunk, the autocorrelation summation values from S(64) to S(127) and samples from X(64) to X(127) are set to zero. Then the total number of summation values, ST, is set to 63. This action shrinks the arrays to one half their prescaling size. If the number of summation values again exceeds 128 (k =127), the scaling factor will be increased by two again and the arrays shrunk in half another time. The shrinking process can be repeated many times until correlation of the incoming data is found or until the maximum limit (e.g. 600) of signal samples is acquired.

Once the arrays of summation values and signal samples have been shrunk and reconfigured, the execution of the serial autocorrelation routine by the digital signal processor 20 terminates until another pulse probe signal sample is stored in the dual ported RAM 19.

If at step 44 the number of previously calculated summation values has not exceeded 128, the effective sampling rate does not have to be changed and the execution of the autocorrelation routine by the digital signal processor 20 advances to step 49. At this point, a determination is made whether the recently acquired sample should be used based on the current effective sampling rate as indicated by the scaling factor $f_T$. If this sample is to be used, a decision is made at step 50 whether the scaling of the signal amplitude needs to be changed because the newest signal sample has exceeded the maximum magnitude that the memory can accommodated with the present scaling factor. For example, the maximum range of values for a digitized signal sample that the digital signal processor can handle ±127, although the digital-to-analog converter 15 produces signal samples with larger digital values which are stored in the dual-ported RAM 19. To make that decision, the new signal sample X(k) is divided by the previous amplitude scaling factor ($f_A$) and the resultant new value for X(k) is checked at step 52 to determine whether it is within the desired magnitude range. Upon reset of the serial autocorrelation process 30, the amplitude scaling factor ($f_A$) is set to one. If the present amplitude scaling factor is not sufficient to bring the new sample within the desired magnitude range, the program execution branches to step 53 where the signal sample X(k) is scaled again by a factor of two. Then at step 54 the amplitude scaling factor ($f_A$) is doubled and stored in the internal memory of the digital signal processor 20. Next, a variable designated LSCALE, which counts the number of times that the amplitude scaling factor is doubled, is incremented at step 55 before a flag is set at step 56 to indicate that the amplitude scaling factor has been changed. The program execution returns to step 52 to determine whether the newly scaled signal sample X(k) is within the desired magnitude range. The program continues to loop through steps 52–56 until the scaled sample X(k) is within the desired range at which point, the program execution branches from step 52 to step 58.

Because the newest signal sample has been scaled by a different factor that used to process than the previously acquired samples and to calculate the previous summation values, the values for those quantities must be adjusted to correspond to the revised amplitude scaling factor. Therefore, at step 58 if the scale flag is set, the values for the previous signal samples are divided by two raised to the power of LSCALE and stored back into memory. At step 60 if the scale flag is set, the previous summation values S(n) are divided by two raised to the power of two times LSCALE. Then at step 62, the scale flag is reset and the value of LSCALE is set to zero for counting any subsequent increases of the amplitude scaling factor which occur at step 54.

The program execution then advances to step 64 where the total number ST of calculated summation values is incremented by one. Next at step 66, new summation values S(0) through S(ST) are derived based on the new signal sample from pulse probe 12. The summation values may be calculated using the following equation:

$$S(n) = f_T (f_A)^2 \sum_{f_Tm=n}^{k} X(f_Tm) \cdot X(f_Tm - n) \qquad (3)$$

where $f_t$ is the time scaling factor and $f_A$ is the amplitude scaling factor. Although the above equation can be solved for each of the summation values to be calculated, the new summation values also can be produced by adding a term for the newest signal sample to each of the previous summation values and solving equation (2) to produce the next summation value S(ST) in the sequence. The execution of the serial autocorrelation routine by the digital signal processor 20 then terminates.

At this point with reference to the processing diagram in FIG. 2, a set of summation values 31 has been produced and stored in the memory of the digital signal processor 20. The monitoring procedure then advances to perform analysis of the autocorrelation at procedure 32.

Figure 6A:
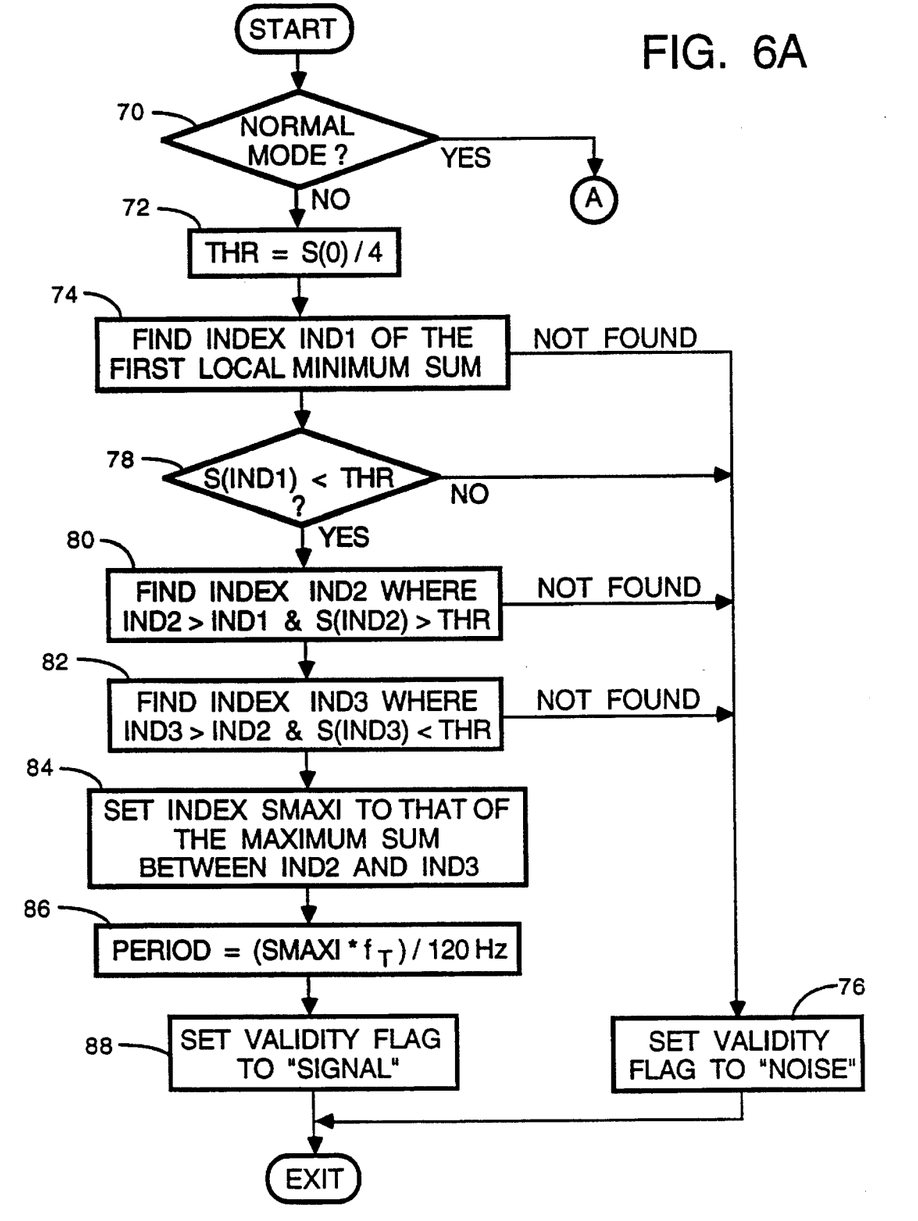
FIGS. 6A and 6B are a flow chart of the autocorrelation analysis performed by the digital signal processor.

With reference to FIG. 6A, the autocorrelation analysis procedure 32 commences at step 70 by the digital signal processor 20 checking another flag to determine whether the analysis has progressed into a NORMAL mode of operation. When the pulse probe 12 is first attached to a patient, the autocorrelation analysis 32 inspects the summation values after each new signal sample is acquired to initially determine the pulse period. Thereafter, once the pulse oximeter 10 is confident that an actual pulse period has been determined, as opposed to a noise induced error, the analysis enters a NORMAL mode. In the NORMAL mode certain processing short cuts, to be described, are utilized which reduce the amount of processing time required by the digital signal processor 20. This enables real-time processing to be performed.

Therefore, initially the autocorrelation analysis will not be in the NORMAL mode and program execution by the digital signal processor 20 jumps to step 72 where a summation value threshold THR is set equal to one-fourth the magnitude of summation value S(0). Then at step 74, the sequence of summation values is inspected to determine the first one which has a local minimum magnitude. This minimum occurs at point 35 in FIG. 4 and can be found using a number of well known techniques. For example, the slope between adjacent summation values can be derived and the slope going positive identifies a local minimum. As can be seen from FIG. 4, initially the summation values will produce a negative slope and the execution of step 74 will not find a local minimum. When that is the case, the analysis routine execution branches to step 76 where a validity flag is set to indicate noise which designates that a valid signal has not been found as yet. The analysis then terminates until another signal sample has been processed into a new set of summation values by the serial autocorrelation process 31.

Eventually enough signal samples will be acquired so that the digital signal processor 20 will find a local minimum summation value at step 74. The summation value at that minimum point 35 is designated S(ind1) where the value of ind1 is the summation value index which corresponds to the number of the signal samples between the initial signal sample S(0) and the signal sample at the minimum point 35.

The program execution then advances to step 78 where a determination is made whether the magnitude of summation value S(ind1) is below the threshold THR. If that is not the case, the validity flag is set to the noise indication at step 78. Otherwise, the digital signal processor 20 advances to step 80 where the summation values with indices greater than ind1 are compared sequentially to the threshold THR to find the next summation value in the sequence with magnitude that is then greater than the threshold THR. Immediately after finding the first local minimum summation value, the summation values with higher indices will have magnitudes below the threshold and the program execution continues to set the validity flag to the noise indication at step 76.

Eventually, a sufficient number of signal samples will be acquired so that a higher indexed summation value will have a magnitude which again goes above the threshold THR as indicated at point 36 in FIG. 4. The corresponding summation value is designated as S(ind2) and has an index ind2. The program then continues to step 82 to locate the next summation value in the sequence which has an index that is greater than ind2 and a magnitude that is below the threshold THR, as occurs at point 37 on the graph of FIG. 4. Until such a summation value is found, the autocorrelation analysis routine continues to set the validity flag to the noise indication at step 76. Eventually, a sufficient number of summation values will be generated such that a summation value S(ind3) will satisfy the test at step 82 causing the analysis routine to advance to step 84. At this point, the summation values between indices ind2 and ind3 are inspected to find the one with the maximum magnitude as indicated at point 38. This maximum summation value is designated as S(MAXI) wherein the index MAXI corresponds to the number of summation values from initial summation value S(0) to the maximum summation value.

This maximum summation value S(MAXI) occurs one pulse period from the commencement of data accumulation at the last reset of the serial autocorrelation. As a consequence, the index MAXI corresponds to the blood pulse period. The time of the blood pulse period in seconds is derived by multiplying index MAXI by the time scaling factor $f_t$ and the product is then divided by the sampling frequency of the analog-to-digital converter 15 (120 Hz.). Then at step 88, the validity flag is set to the "signal" indication before the autocorrelation analysis terminates.

The results of the autocorrelation analysis procedure 32 (FIG. 2) are provided to the confidence level determination process 34 which sets the mode of operation and determines the relative confidence in the accuracy of the blood pulse period measurement. The analysis of the autocorrelation summation values determines whether the present pulse probe signal has been corrupted with excessive noise so as to be unreliable for use in determining the pulse period and rate. For example, if the finger to which the pulse probe 12 is attached moves, motion artifacts will be introduced into the pulse probe signal which could otherwise be interpreted as resulting from a blood pulse and thereby produce and erroneous pulse period and rate.

Initially, the confidence level determination process 34 is in the START mode, until a pulse period has been determined. Then the process enters the CONFIRM mode until sufficient information about the signal has been collected to ensure that the determined period indeed represents the blood circulation pulse period and did not result from signal noise. Thereafter, the process assumes a NORMAL, mode of operation.

Figure 7:
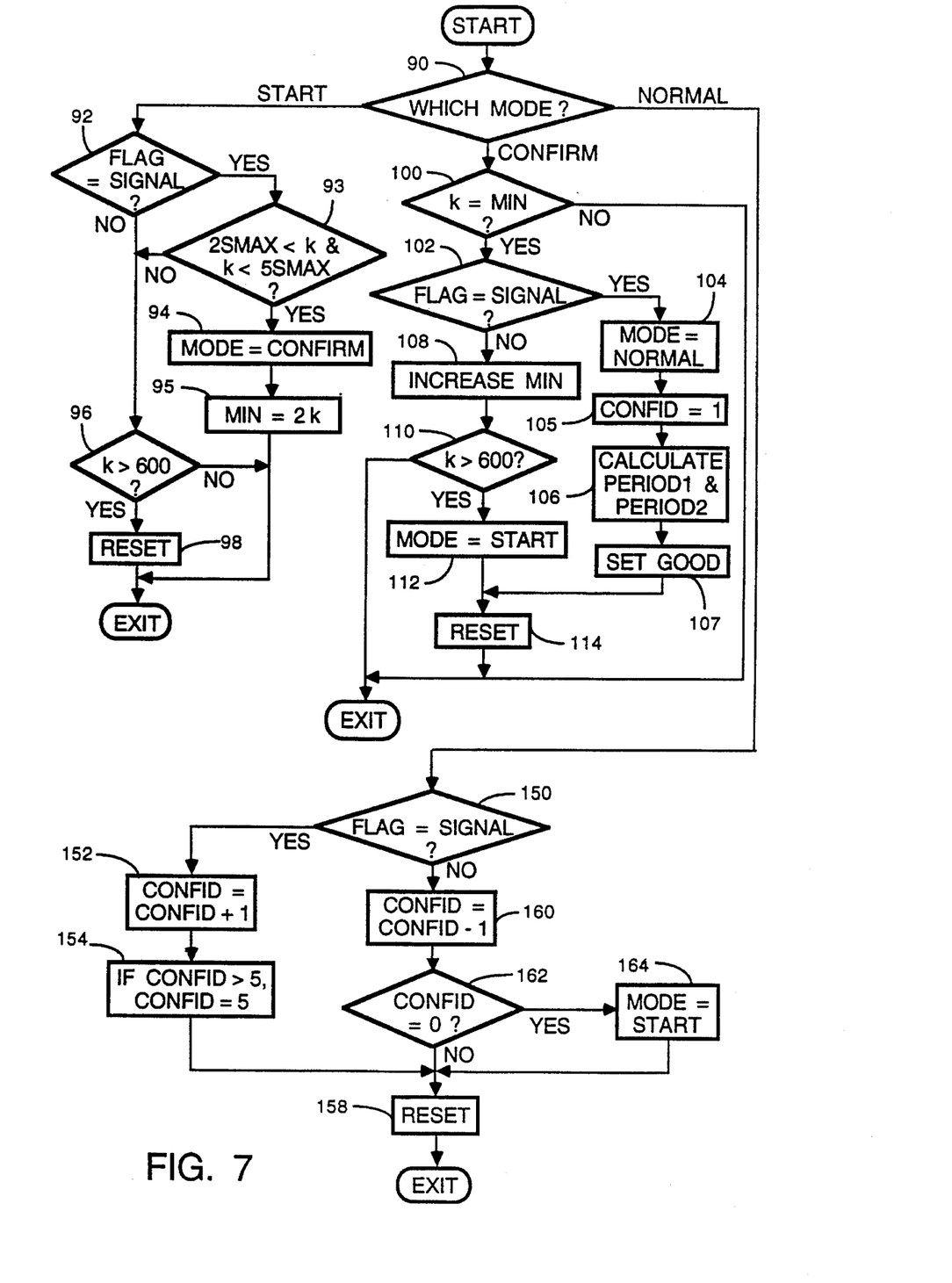
FIG. 7 is a flow chart of a confidence level determination which is part of the monitoring procedure.

Referring to FIG. 7, when a new value for the pulse period has been derived, the confidence level determination process is executed and commences at step 90 by determining the present mode of the autocorrelation process. Initially, the START mode will be active and the program execution branches to step 92 where the validity flag is inspected to determine whether it indicates a legitimate "signal" has been processed by the autocorrelation analysis procedure 32. If that is the case, a check is made at step 93 whether a sufficient number of signal samples have been acquired. For example, the number of signal samples must be more than twice the index MAXI of the maximum summation value used to determine the pulse period and less than five times index MAXI. Once a sufficient number of samples has been acquired, the mode is changed to CONFIRM at step 94 and a minimum limit MIN for the number of signal samples is set equal to two times the number k of acquired signal samples, at step 95.

If the test at either step 92 or 93 fails, the program execution branches to step 96 where a determination is made whether 600 signal samples have been acquired since the last reset of the serial autocorrelation. As previously noted, 600 samples corresponds to a blood pulse rate of approximately 30 beats per minute which is well below the level required to keep a human alive. If that number of signal samples has not been acquired, the routine terminates; whereas a greater amount of signal samples has been acquired the RESET indicator is set true at step 98.

Eventually, as described above, a sufficient number of signal samples will be processed so that a pulse period is determined by the autocorrelation analysis procedure 32 which causes the confidence level determination routine to advance to the CONFIRM mode. It should be noted that in the START and CONFIRM modes, the pulse oximeter 10 does not display the pulse period, but merely produces an output indicating that a reliable determination has yet to be made.

When the physiological monitoring procedure advances to the CONFIRM mode, the execution of the confidence level determination routine in FIG. 7 branches from step 90 to step 100 where a decision is made if the number of signal samples k which has been acquired since the last reset of the procedure, exceeds the minimum limit designated MIN set previously at step 95. If the sample limit has not been reached, the execution by the digital signal processor 20 terminates and continues to do so at step 100 until that minimum number of samples has been acquired.

When enough signal samples exist, the program execution advances to step 102 where the validity flag is inspected to ensure that a valid signal is being processed, as compared to noise. If the validity flag indicates that the signal samples are contaminated by noise, the program execution branches to step 108 where the value of MIN is increased. Then a determination is made at step 110 whether the maximum number (600) of signal samples have been evaluated by the autocorrelation process. If less than that number of samples have been processed, the confidence level determination process 34 terminates. Otherwise, the digital signal processor 20 advances to step 112 where the physiological monitoring procedure returns to the START mode before the RESET indicator for the serial autocorrelation process is set true at step 114.

When a sufficient number of valid signal samples have been processed as determined by steps 100 and 102, the physiological monitoring enters the NORMAL mode at step 104. Then a variable designated CONFID, which numerically indicates a confidence level of between one and five, is set to one at step 105. The higher the value of the indicator variable CONFID, the greater the confidence level in the accuracy of the determined pulse period. Then at step 106, values for variables PERIOD1 and PERIOD2 are calculated as follows: PERIOD1=⅔ *pulse period and PERIOD2 =1.5 *pulse period. As will be described this pair of variables defines a range of sums within which subsequent maximum summation values are likely to be found. Next, at step 107 an procedure output indicator is set to "GOOD" thereby providing an indication that the pulse period produced by the serial autocorrelation process now is valid.

The next pulse probe signal sample stored in the dual-ported RAM 19 by the primary microcomputer 16 will be processed with the physiological monitoring procedure operating the NORMAL mode. In this mode, the serial autocorrelation process 30 is performed as described for the previous modes. However, when the new set of summation values 31 is generated, the autocorrelation analysis procedure 32 operates differently in the NORMAL mode. Now the autocorrelation analysis commences by branching to step 120 in FIG. 6B. At this point, a new value for the summation value threshold THR is derived by dividing the present value of initial summation value S(0) by four. Then, at step 122, summation values in the sequence up to an index of PERIOD1 are inspected to locate the first summation value that is below threshold THR. It is noted that in the NORMAL mode such a summation value will not be found initially after reset of the autocorrelation-process 30. If this summation value is not found, the program execution branches to step 124 where the validity flag is set to the "noise" indication. Once a summation value below the threshold THR is found, a variable IND1 is set equal to the index of that summation variable as depicted on the graph of FIG. 8. The program execution then advances to step 126 where the absolute maximum summation value between indices ind1 and PERIOD1 is found. Theoretically, this first absolute maximum value should occur at ind1. If not, noise may be present on the signal which produces a different location for the maximum value. Then at step 128, a variable designated SMAXX is set to the magnitude of the first absolute maximum summation value.

Figure 8:
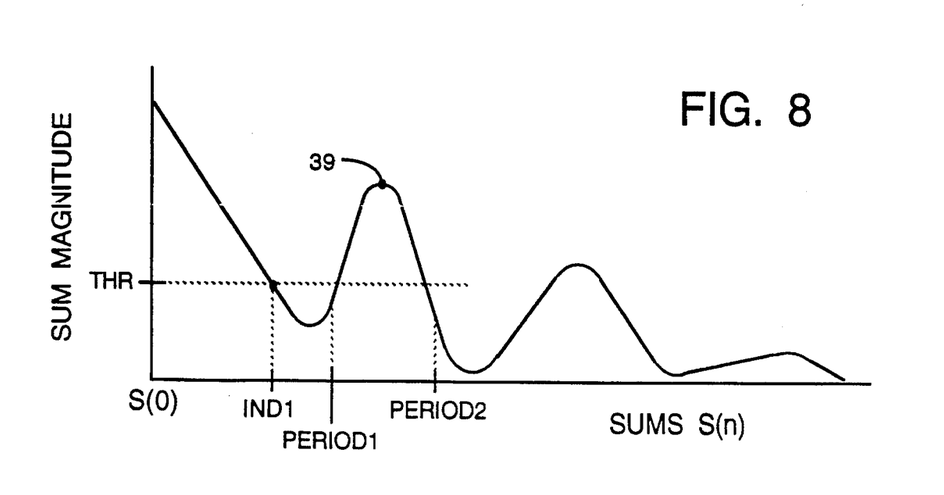
FIG. 8 is a graph of the intermediate results of the physiological monitoring which shows processing benchmarks.

At step 130, the digital signal processor 20 in executing the autocorrelation analysis routine finds the absolute maximum summation value between indices PERIOD1 and PERIOD2 as indicated at point 39 in FIG. 8. The value of this second maximum summation value is stored as variable SMAX at step 132 and the second maximum summation value's index is stored as variable SMAXI at step 134.

Figure 6B:
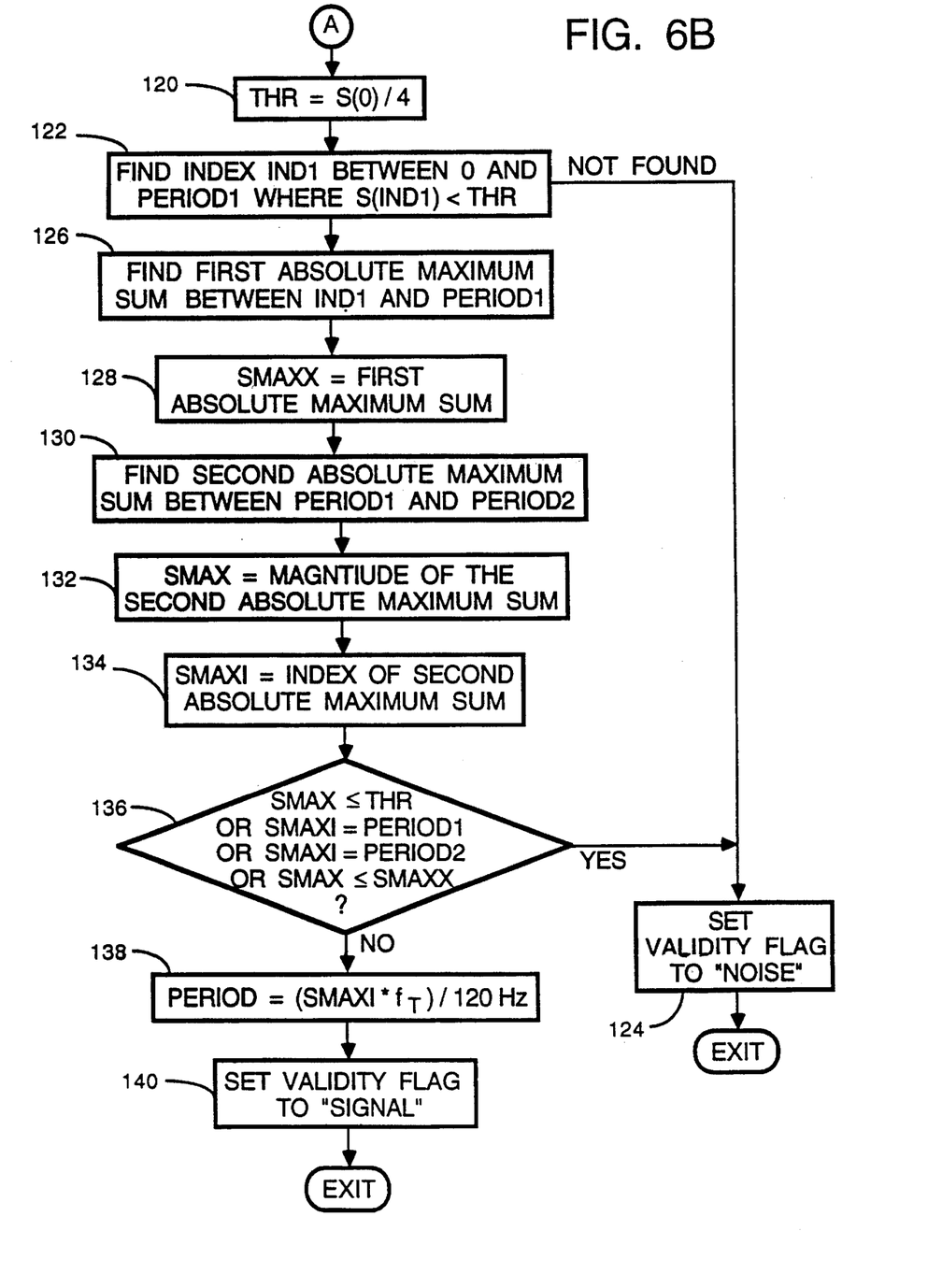

The validity of this second maximum summation value as corresponding to one pulse period from index zero is determined at step 136. The maximum summation value will be invalid for this purpose if the second absolute maximum summation value SMAX is less than or equal to the threshold THR, or index SMAXI is equal to PERIOD1 or PERIOD2, or SMAX is less than or equal to the first absolute maximum summation value SMAXX. If any of these conditions exists, the validity flag is set to indicate "noise" rather than a valid "signal" at step 124.

If step 136 determines that a valid maximum summation value has been found, the performance of the autocorrelation analysis process by the digital signal processor 20 advances to step 138 where the blood pulse period is derived by multiplying the index SMAXI of the maximum summation value, by the time scaling factor $f_t$ and then dividing that product by the sampling frequency (120 Hz.) of analog-to-digital converter 15. The value of the blood pulse period is then made available to the confidence level determination process 34 along with the validity flag which at step 140 indicates that a good "signal" exists.

The digital signal processor 20 then begins the confidence level determination process 34 which commences at step 90 shown in FIG. 7 and immediately branches in the NORMAL mode to step 150. A check is made whether the validity flag that was set to indicate a good signal. If that is the case, the program execution branches to step 152 where the confidence level indication variable CONFID is incremented by one. This variable indicates the confidence that the physiological monitoring procedure has in the determined blood pulse period and has values ranging from zero to five. Thus, if at step 154 variable CONFID is found to be greater than five, it is reset to the maximum value. The execution of the confidence level determination process 34 then sets the RESET indicator for the serial autocorrelation process at step 158 before terminating.

If upon commencement of the confidence level determination process 34 in the NORMAL mode the validity flag indicates "noise" at step 150, the digital signal processor 20 decrements the confidence level indication variable CONFID by one at step 160. A determination then is made at step 162 whether that CONFID has reached zero, thereby indicating that the determined blood pulse period may be inaccurate. If CONFID has a zero value, the physiological monitoring procedure is returned to the START mode at step 164 before issuing a RESET indication at step 158.

As shown in FIG. 2, the confidence level determination process 34 produces three outputs. The first output, designated PERIOD, is the numerical value of the blood circulation pulse period. Another output is a flag indicating whether the results are good or bad which is set to the good indication only in the NORMAL mode of operation. The third output is the confidence level having a numerical value between zero and five. Upon completion of the confidence level determination process 34, the digital signal processor 20 stores the output values of these three variables in assigned locations within dual ported RAM 19.

The primary microcomputer 16 is able to access these output values. If the data is indicated as being bad or a zero confidence level exists, the primary microcomputer 16 provides a warning indication via the display 17 to the user of the oximeter 10. On the other hand, if the data indicates that the blood pulse period value is valid, the primary microcomputer 16 uses that period to calculate the pulse rate and then displays the resultant value to the user via display 17.

I claim:

1. A method performed by a medical monitor in order to determine a period of a physiological function of a patient, wherein the method comprises steps of:

operating a probe to produce an electrical signal which represents the physiological function;

periodically sampling the electrical signal at a given sampling rate to acquire a plurality of signal samples X(i), where i is an integer that designates a particular signal sample;

storing the plurality of signal samples in a memory;

applying serial autocorrelation to the plurality of signal samples to produce a sequence of summation values S(n), where n is a positive integer which designates a particular summation value and an order of the summation values in the sequence;

storing the sequence of summation values in the memory;

locating a peak summation value S(max), where max is a positive integer, by:
 (a) deriving a threshold value,
 (b) locating a first summation value S(ind1) which has a magnitude that is less than the threshold value and where ind1 is a positive integer,
 (c) locating a second summation value S(ind2) having a magnitude greater than the threshold value and where ind2is a positive integer greater than ind1,
 (d) locating a third summation value S(ind3) having a magnitude less than the threshold value and where ind3is a positive integer greater than ind2, and
 (e) then locating the peak summation value S(max) as a summation value of greatest magnitude that is between the second and third summation values;

determining a count of summation values in the sequence of summation values from an initial summation value to the peak summation value S(max); and deriving the period from the count of summation values and the given sampling rate.

2. The method as recited in claim 1 wherein the step of applying serial autocorrelation produces each of the summation values S(n) according to the function:

$$S(n) = f \sum_{i=n}^{k} X(i) \cdot X(i-n)$$

where f is a scaling factor and k is the amount of signal samples that have been accumulated since a previous reset of the serial autocorrelation.

3. The method as recited in claim 1 further comprising evaluating whether the plurality of signal samples accurately represent the physiological function by producing an invalidity indication if the first summation value S(ind1) is not located.

4. A method performed by a medical monitor in order to determine a period of a physiological function of a patient, wherein the method comprises steps of:

operating a probe to produce an electrical signal which represents the physiological function;

periodically sampling the electrical signal at a given sampling rate to acquire a plurality of signal samples X(i), where i is an integer that designates a particular signal sample;

storing the plurality of signal samples in a memory;

applying serial autocorrelation to the plurality of signal samples to produce a sequence of summation values S(n), where n is a positive integer which designates a particular summation value and an order of the summation values in the sequence;

storing the sequence of summation values in the memory;

locating a peak summation value S(max), where max is a positive integer;

determining a count of summation values in the sequence of summation values from an initial summation value to the peak summation value S(max);

deriving the period from the count of summation values and the given sampling rate;

locating a first summation value S(period1) where period1 is an integer less than max; and locating a second summation value S(period2) where period2 is an integer greater than max.

5. The method as recited in claim 4 wherein period1 is substantially equal to two-thirds of max; and period2 is substantially equal to 1.5 times max.

6. The method as recited in claim 4 further comprising deriving a threshold value; and locating a summation value S(ind1) which is first to occur in the sequence with a magnitude that is less than the threshold value, where ind1 is a positive integer.

7. The method as recited in claim 6 further comprising indicating whether the plurality of signal samples accurately represent the physiological function by producing an invalidity indication when at least one of the following conditions exists:

(a) the summation value S(ind1) could not be located, (b) a summation value of greatest magnitude between S(ind1) and S(period1) has a magnitude less than the threshold value, (c) S(period1) is a summation value of greatest magnitude between period1 and period2 inclusive, (d) S(period2) is the summation value of greatest magnitude between period1 and period2 inclusive, and (e) the summation value of greatest magnitude between S(period1) and S(period2) inclusive is less than the summation value of greatest magnitude between S(ind1) and S(period1);

otherwise producing a validity indication.

8. The method as recited in claim 7 further comprising incrementing a confidence indication whenever the validity indication is produced, and decrementing the confidence indication whenever the invalidity indication is produced.

9. A method performed by a medical monitor in order to determine a period of a physiological function of a patient, wherein the method comprises steps of:

operating a probe to produce an electrical signal which represents the physiological function;

periodically sampling the electrical signal at a given sampling rate to acquire a plurality of signal samples X(i), where i is an integer that designates a particular signal sample;

storing the plurality of signal samples in a memory;

applying serial autocorrelation to the plurality of signal samples to produce a sequence of summation values S(n), where n is a positive integer which designates a particular summation value and an order of the summation values in the sequence;

storing the sequence of summation values in the memory;

locating a peak summation value S(max), where max is a positive integer;

when the peak summation value S(max) can not be located within a predefined amount of summation values, then increasing a time scaling factor $f_T$ by two, shrinking the sequence of summation values by one-half, and disregarding every other previously acquired signal sample in subsequent production of summation values;

determining a count of summation values in the sequence of summation values from an initial summation value to the peak summation value S(max); and deriving the period from the count of summation values and the given sampling rate.

10. The method as recited in claim 9 wherein the step of deriving the period comprises the count of summation values multiplied by the given sampling rate divided by the time scaling factor.

11. A method performed by a medical monitor in order to determine a period of a physiological function of a patient, wherein the method comprises steps of:

operating a probe to produce an electrical signal which represents the physiological function;

periodically sampling the electrical signal at a given sampling rate to acquire a plurality of signal samples X(i), where i is an integer that designates a particular signal sample;

storing the plurality of signal samples in a memory;

applying serial autocorrelation to the plurality of signal samples to produce a sequence of summation values S(n), where n is a positive integer which designates a particular summation value and an order of the summation values in the sequence;

storing the sequence of summation values in the memory;

locating a peak summation value S(max), where max is a positive integer;

when a signal sample exceeds a predetermined magnitude, doubling an amplitude scaling factor $f_A$, dividing each previously acquired signal sample by two, dividing each of the sequence of summation values produced previously by four, and dividing each signal sample acquired thereafter by the amplitude scaling factor $f_A$;

determining a count of summation values in the sequence of summation values from an initial summation value to the peak summation value S(max);

deriving the period from the count of summation values and the given sampling rate.

12. The method as recited in claim 11 further comprising, when the peak summation value S(max) can not be located with in a predefined amount of summation values:

increasing a time scaling factor $f_T$ by two;

shrinking the sequence of summation values by one-half; and disregarding every other previously acquired signal sample in subsequent production of summation values.

13. The method as recited in claim 12 wherein the step of applying serial autocorrelation produces each of the sequence of summation values S(n) according to the function:

$$S(n) = f_T f_A^2 \sum_{f_T m=n}^{k} X(f_T m) \cdot X(f_T m - n)$$

where k is the quantity of signal samples that have been accumulated since a previous reset of the serial autocorrelation.

14. A medical apparatus for monitoring a physiological function of a patient, wherein the medical apparatus comprises:

a probe for sensing the physiological function and producing an electrical signal indicative thereof;

a converter connected to said probe to sample the electrical signal at a given sampling rate and produce a plurality of signal samples X(i), where i is an integer that designates a particular signal sample;

a first memory which receives and stores the plurality of signal samples produced by said converter;

a mechanism that applies serial autocorrelation to the plurality of signal samples to produce a sequence of summation values S(n), where n is a positive integer which designates a particular summation value and an order of the summation values in the sequence;

a second memory which stores the sequence of summation values produced by said mechanism;

a means for locating a peak summation value S(max) produced by said mechanism, where max is a positive integer;

a means for determining a count of summation values in the sequence from an initial summation value in the sequence to the peak summation value S(max);

a means for deriving a period of the physiological function from the count of summation values and the given sampling rate;

means for increasing a time scaling factor $f_T$ by two;

means for disregarding every other signal sample stored in the first memory; and means for shrinking the sequence of summation values stored in the second memory by one-half.

15. The medical apparatus as recited in claim 14 wherein the means for deriving the period multiplies the count of summation values by the given sampling rate divided by the time scaling factor.

16. A medical apparatus for monitoring a physiological function of a patient, wherein the medical apparatus comprises:

a probe for sensing the physiological function and producing an electrical signal indicative thereof;

a converter connected to said probe to sample the electrical signal at a given sampling rate and produce a plurality of signal samples X(i), where i is an integer that designates a particular signal sample;

a first memory which receives and stores the plurality of signal samples produced by said converter;

a mechanism that applies serial autocorrelation to the plurality of signal samples to produce a sequence of summation values S(n), where n is a positive integer which designates a particular summation value and an order of the summation values in the sequence;

a second memory which stores the sequence of summation values produced by said mechanism;

a means for locating a peak summation value S(max) produced by said mechanism, where max is a positive integer;

a means for determining a count of summation values in the sequence from an initial summation value in the sequence to the peak summation value S(max);

a means for deriving a period of the physiological function from the count of summation values and the given sampling rate;

means for doubling an amplitude scaling factor $f_A$;

means for dividing each signal sample stored in said first memory by two;

means for dividing each summation value stored in said second memory by four; and means for dividing each signal sample from the converter by the amplitude scaling factor $f_A$.

17. The medical apparatus as recited in claim 16 further comprising:

means for increasing a time scaling factor $f_T$ by two;

means for disregarding every other signal sample stored in the first memory; and means for shrinking the sequence of summation values stored in the second memory by one-half.

18. The medical apparatus method as recited in claim 17 wherein the step of applying serial autocorrelation produces each of the sequence of summation values S(n) according to the function:

$$S(n) = f_T f_A^2 \sum_{f_T m=n}^{k} X(f_T m) \cdot X(f_T m - n)$$

where k is a count of signal samples stored in said first memory.

* * * * *